(12) United States Patent
Farberov

(10) Patent No.: US 8,011,504 B1
(45) Date of Patent: Sep. 6, 2011

(54) DISPOSABLE STERILE PROTECTIVE COVER FOR OPTICAL DEVICES USED IN OPHTHALMOLOGY

(76) Inventor: Arkadiy Farberov, Fremont, CA (US)

(*) Notice: Subject to any disclaimer, the term of this patent is extended or adjusted under 35 U.S.C. 154(b) by 0 days.

(21) Appl. No.: 12/928,152

(22) Filed: Dec. 6, 2010

(51) Int. Cl.
*B65D 85/38* (2006.01)
(52) U.S. Cl. ........................ 206/316.1; 206/363; 206/438
(58) Field of Classification Search .................. 206/438, 206/439, 440, 363; 150/154, 165
See application file for complete search history.

(56) References Cited

U.S. PATENT DOCUMENTS

| | | | | |
|---|---|---|---|---|
| 2,869,606 A * | 1/1959 | Jennings | ........................ | 379/451 |
| 3,320,812 A * | 5/1967 | Taylor et al. | .................... | 73/431 |
| 4,045,118 A * | 8/1977 | Geraci | ........................ | 359/510 |
| 4,561,540 A * | 12/1985 | Hunter et al. | ........................ | 209/305 |
| 5,036,446 A * | 7/1991 | Quintanilla et al. | .......... | 362/399 |
| 5,113,863 A * | 5/1992 | Herman | ........................ | 600/405 |
| 5,282,470 A * | 2/1994 | Cohen et al. | .................. | 600/405 |
| 5,355,292 A * | 10/1994 | Hoftman et al. | .............. | 362/400 |
| 5,537,164 A | 7/1996 | Smith | | |
| 5,954,646 A * | 9/1999 | Jost et al. | ....................... | 600/406 |
| 6,082,535 A * | 7/2000 | Mitchell | ........................ | 206/320 |
| 6,318,864 B1 * | 11/2001 | Fukaya et al. | ................ | 359/510 |
| 6,514,241 B1 | 2/2003 | Hsia et al. | | |
| 6,767,098 B2 | 7/2004 | Erickson et al. | | |
| 6,942,343 B2 | 9/2005 | Farberov | | |
| 6,945,936 B1 * | 9/2005 | Kerr | ............................ | 600/406 |
| 7,125,119 B2 | 10/2006 | Farberov | | |
| 7,144,111 B1 | 12/2006 | Ross, III et al. | | |

* cited by examiner

*Primary Examiner* — Jacob K Ackun

(57) ABSTRACT

The device of the invention comprises a protective cover for an optical device such as a gonioscope, capsulatomy lens, wide-angle lens, or any other lens having an eye-contacting surface. The cover is made sterile and disposable for allowing multiple use of the protected optical device. The cover is made from a soft material biologically acceptable for contact with a human eye. According to one aspect, the gonioscope protective cover is used merely for physically protecting the eye-contacting surface from direct contact with the eye. According to another aspect, the gonioscope protective cover combines the protective function with an optical function that changes the direction of light so that it becomes possible to observe the light emitted from the pupil at angles that are close to the angle of full internal reflection from the pupil medium.

11 Claims, 5 Drawing Sheets

DISPOSABLE STERILE PROTECTIVE COVER FOR OPTICAL DEVICES USED IN OPHTHALMOLOGY

FIELD OF THE INVENTION

The present invention relates to optical devices used in ophthalmology for intraocular observation, diagnosis, treatment, or the like, especially for angled portions, of an eyeball. In particular, the invention relates to a disposable, sterile protective cover for protecting eye-contacting lenses of aforementioned devices from physical contact with a patient's eye during intraocular observation or treatment. The use of such a disposable cover eliminates the sterilization process.

BACKGROUND OF THE INVENTION

Diagnostic and therapeutic lenses are commonly used in ophthalmology for evaluation and treatment of the internal portions of the eye. In order to effect treatment for a variety of ocular disorders, an ophthalmologist must first see the inner structure of the eye. After an appropriate examination is completed, a laser delivery system may be used, e.g., to thermally heat the appropriate anatomical structures within the eye with laser light. Prior technology often includes a slit lamp biomicroscope used in conjunction with specialized ophthalmic instruments (devices) and special eye-contacting lenses. These lenses are designed to view different anatomical areas within the eye. The patient's pupil is usually pharmacologically dilated, topical anesthesia is placed on the eye, a coupling agent is placed on the posterior surface of the lens, and the examiner holds the lens over the surface of the eye.

During use, the instruments of the aforementioned type are brought in direct contact with the cornea of the patient's eye. In order to prevent transfer of infections from patient to patient, such optical instruments, especially the eye-contacting portions thereof, must be properly sterilized before use. The sterilization procedure most widely used in practice is treatment in an autoclave. However, since sterilization in an autoclave is a high-temperature procedure, such treatment may be undesirable for optical instruments that have optical materials, bondings, and coatings degradable under the effect of high temperatures.

Devices used in ophthalmology for intraocular observations include a line of wide-angle lenses, gonio lenses, capsulatomy and iridectomy lenses, laser photocoagulation lenses, etc.

Observation of the anterior chamber and especially its angled areas, which are difficult or impossible to see with the use of some conventional optical means, is very important for diagnosis of eye diseases. For example, the classification of glaucoma relies heavily on knowledge of anterior segment anatomy, particularly that of the anterior chamber angle.

The anterior chamber of a human eye is commonly evaluated during slit lamp biomicroscopy, but the chamber angle is hidden from ordinary view because of total internal reflection of light rays emanating from the angled structures. In other words, without gonioscopy, additional diagnostic clues of disease are forever hidden from ordinary view. Additional effort, skill, and patient cooperation are required to view the normally concealed chamber angle by either indirect (angled structures viewed through a mirror) or direct (angled structures viewed directly) gonioscopic techniques. In other words, without gonioscopy, it is impossible to classify glaucoma properly.

An example of a typical, solid, i.e., monolithic, gonioscope is shown in U.S. Pat. No. 6,767,098 issued in 2004 to Ph. Erickson, et al. The gonioscope has an optically transparent body, the distal end has a viewing surface preferably oriented perpendicularly to the optical axis of the body, the proximal end of the prism has a concave surface with a curvature similar to the curvature of a patient's cornea. The proximal end has at least one planar surface extending outwardly and distally from a location adjacent to the periphery of the concave surface. The body has an index of refraction that provides total internal reflection to a viewer looking through the viewing surface even when the planar surface is at least partially moistened with a fluid.

Common to wide-angle lenses, gonio lenses, capsulatomy and iridectomy lenses, and laser photocoagulation lenses is the provision of an eye-contacting lens that during observation or surgical treatment is maintained in physical contact with the eye cornea. Such optical devices require sterilization after use, especially with regard to the eye-contacting surfaces and especially when the optical device is intended for surgical use.

SUMMARY OF THE INVENTION

The device of the invention comprises a sterile, disposable protective cover made from a soft optical material such as organic polymer, rubber, etc., that is capable of conforming to the shape of the portion of an instrument that directly contacts a patient's eye. The protective cover comprises an elastic body that has a shape conforming to the shape of the ophthalmologic lens for protection of which it is intended. The protective cover is made from an optically transparent thin elastic material such as optically clear polyurethanes, isoprenes, polyisobutylenes, and optically clear silicone elastomers, which have an appropriate refraction index and satisfy all other conditions mentioned above. For example, the optically clear silicone elastomer MED-6020 (the product of NuSil technology, USA) has a refraction index of 1.41, a durometer type-A hardness of 40, a tensile strength of 640 psi, and an elongation of 175%. A relatively high refractive index of the material for the bottom portion makes it possible to observe the anterior chamber of the eye, which is very important for diagnosing glaucoma.

One end of the cover is open for insertion of the optical device, and the opposite end, which covers the eye-contacting lens of the optical device, is closed. In a free state, the diameter of the protective cover is smaller than the outer diameter of the optical device so that when the optical device is inserted into the protective cover, the material tightly embraces the side surfaces of the optical device. However, a gap must be left between the closed end of the protective cover and the eye-facing surface of the eye-contacting lens in order to allow the material of the closed end of the cover to deform and to accommodate a gapless position between the concave surface of the eye-contacting lens and the substantially spherical surface of the eye.

Since air may be trapped in the space between the closed end of the protective cover and the facing surface of the eye-contacting lens, small holes can be provided in the sides of the closed end of the cover for release of trapped air. These holes should be made in positions that exclude contact of the perforated area of the cover with the surface of the eye or with any fluid emitted from the eye during observation or treatment. In other words, when the cover is in a working position on the patient's eye, the perforated area of the closed end of the cover assumes a position above the eye-contacting lens.

According to one aspect of the invention, the sterile protective cover is used merely for physically protecting the eye-contacting lens of the optical device from direct contact with the eye. This protective cover has a uniform thickness in the range from 10 µm to 100 µm. Since the closed end portion of this protective cover has a thickness in the range of 10 µm to 100 µm, the refraction of light that occurs when the beam passes through this portion of the cover can be neglected because the refraction of light will not affect the optical path of light. In the optical lens of this modification, the bottom portion of the elastic cover is molded flat so that it becomes flat under the effect of stretching forces that occur when the disposable sterile protective cover is fitted onto the optical device prior to contact with the eye.

According to another aspect of the invention, the protective cover combines the protective function with an optical function that changes the direction of the light so that, e.g., for a gonioscope, it becomes possible to observe the light emitted from the pupil at angles that are smaller but close to the angle of full internal reflection from the pupil medium. This makes it possible to observe the anterior chamber of the eye, which is very important for diagnosing glaucoma. The protective cover of this type may have thin side portions, e.g., of the same thickness as the protective cover of the previous modification, but the bottom portion of the cover is thickened to a value sufficient for changing the direction of light due to refraction of light through this bottom portion so as to direct the light to the hard-to-observe area of eye, such as the anterior chamber of the eye. In order to provide a high index of refraction in combination with softness required for conforming to the patient's eye and low light absorption, it is recommended to manufacture the protective cover from such materials as optical polyurethane, isoprene, and optically clear silicone elastomer. Regarding this modification, the sterile protective cover is used as an additional optical component of an ophthalmological instrument that makes it possible to adjust optical properties of the instrument, i.e., to change the optical path of the beam inside the eye, to observe hard-to-reach areas inside the eye, etc.

If materials are not biologically acceptable, their surfaces can be coated with a superthin layer (e.g., 2 to 5 µm) of Teflon™ (DuPont) that is chemically neutral and is accepted even for coating body implants.

DETAILED DESCRIPTION OF THE INVENTION

Figure 1:
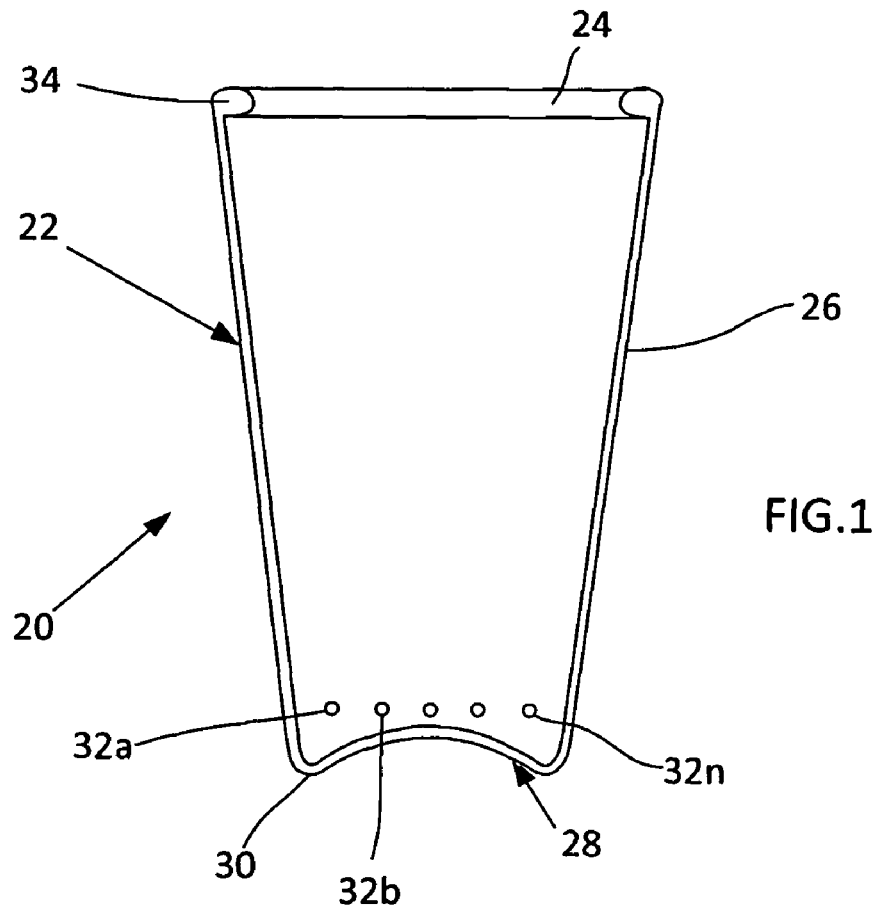
FIG. 1 is a longitudinal and sectional view of a protective cover according to the first aspect of the invention, wherein the entire cover has a uniform thickness.

The device of the invention is intended to protect the eye-contacting lens of an ophthalmological optical device from contact with the eye during observation or treatment. The device of the invention comprises a sterile protective cover 20 (hereinafter referred to as a protective cap), shown in FIG. 1, which is a longitudinal and sectional view of the cover 20. The protective cap 20 is intended for keeping the surface of the eye-contacting lens from physical contact with the eye. During use of the optical device, the eye-contacting lens contacts the eye through the material of the protective cover. For this purpose, the protective cover 20 is made from a soft optical material capable of conforming to the shape of the object with which it is brought into contact. Recommended materials are optically transparent thin elastic materials such as optically clear polyurethanes, isoprenes, polyisobutylenes, and optically clear silicone elastomers, which have a sufficiently high refraction index and satisfy all other conditions mentioned above. One example is the optically clear silicone elastomer MED-6020 (product of NuSil technology, USA), which has a refraction index of 1.41, a durometer type-A hardness of 40, a tensile strength of 640 psi, and an elongation of 175%.

The protective cover comprises an elastic cup-shaped body 22 that has an open upper end 24, a side wall 26, and a closed bottom portion 28. At its open end, the inner diameter of the elastic cup-shaped body 22 is preferably smaller than the outer diameter of the respective part of the optical device (not shown in FIG. 1) in order to provide a tight fit of the side wall 26 of the protective cover 20 with the outer surface of the optical device. Such tight fit is possible because of the resiliency of the elastic cup-shaped body.

The closed bottom portion 28 is made from a transparent material that is biologically acceptable for contact with the cornea (not shown) when the optical device is brought into contact with the eye through the closed bottom portion 28.

The surface area of the closed bottom portion 28 should provide conformity of this portion with the cornea of the eye when the bottom portion 28 is brought in contact with the patient's eye. More specifically, it is known that the radius of the cornea R is approximately 7±0.5 mm. Therefore, the surfaces of the eye-contacting lenses of respective optical instruments have approximately the same radius of 7±0.5 mm. In view of the above, the diameter of the closed bottom portion should be approximately 15 mm. In reality, the cornea sphere may have deviations from regular sphericity, e.g., in astigmatism. In order to compensate for such deviations, an ophthalmologist applies an intermediate liquid to the cornea surface. Partially, such deviations are also compensated by softness and elasticity of the cover material.

Figure 2:
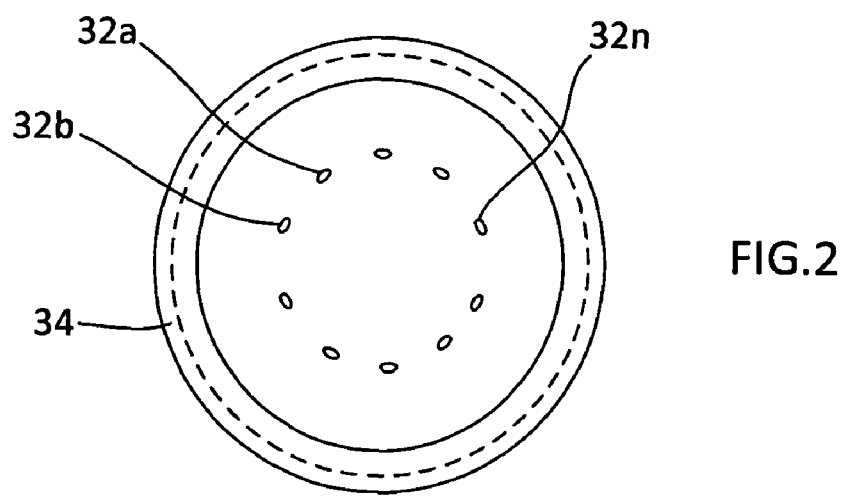
FIG. 2 is a top view of the protective cover in FIG. 1.

The closed bottom portion 28 of the cup-shaped body 22 has an end face 30 intended for contact with the eye and at least one perforation above the end face 30. In FIG. 1, a plurality of such perforations 32a, 32ab, . . . 32n are shown. As shown in FIG. 2, which is a top view of the protective cover 20, the protective cover has perforations 32a, 32b, 32n that are arranged in a circular direction above the end face 30 in the area that excludes contact of these perforations with the surface of the eye cornea or with any fluid that may be present on the surface of the cornea during observation or treatment of the eye with the use of the respective optical device.

As shown in FIGS. 1 and 2, the protective cover 20 may be provided with a cover holding means 34 formed on the edge of the open upper end 24 for securing the protective cover to the optical device (not shown in FIGS. 1 and 2). Such cover holding means may comprise, e.g., a resilient toroidal ring that constitutes a thickened portion of the resilient material of the cup-shaped body 22. Alternative, the cover holding means 34 may comprise a cylindrical helical spring formed into a toroidal ring by connecting two ends of the spring. If necessary, other means, e.g., a resilient rubber string, can be used for attachment of the open upper end 24 of the cup-shaped body 22, e.g. to the yoke of the optical device.

The protective cover is stored in a sterile and sealed pack (not shown) in a flat form that is obtained by coiling the cup-shaped body into annular configuration around the toroidal ring 34. Prior to use, the pack is opened, the sterile protective cover is uncoiled into the cup-shaped form shown in FIG. 1 and is fitted onto the optical device, in this case, gonioscope 36, in the manner shown in FIG. 3.

Figure 3:
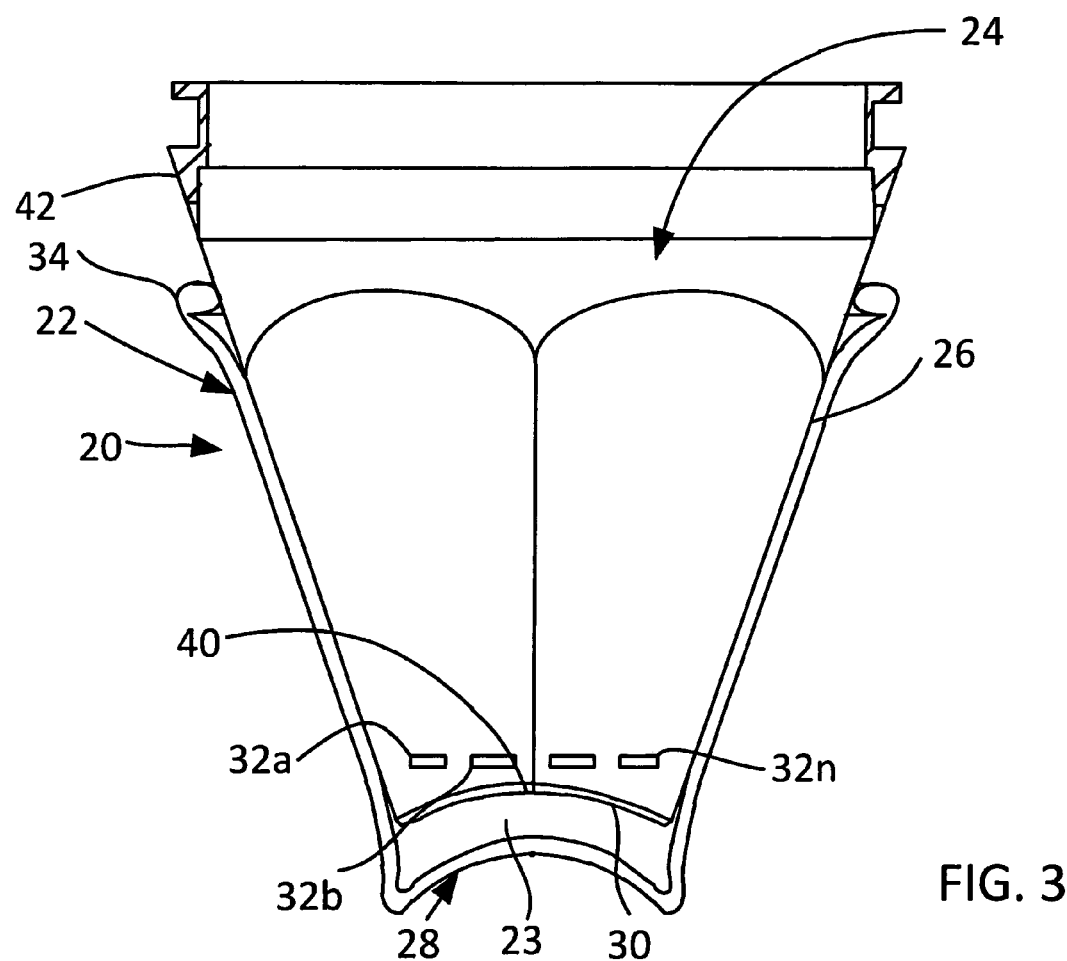
FIG. 3 is a longitudinal sectional view of the protective cover in FIGS. 1 and 2 that is tightly fitted onto the outer surface of the ophthalmological optical device shown in the form of a solid gonioscope.

FIG. 3 is a longitudinal and sectional view of the protective cover 20 tightly fitted onto the outer surface of an ophthalmological optical device 36 shown in the form of a solid gonioscope. The gonioscope 36 has side facets (only two of which, i.e., facets 38a and 38b, are shown in FIG. 3) and an eye-contacting lens 40 formed on the lower end of the gonioscope and facing the inner surface of the closed bottom portion 28 of the protective cover 22. It can be seen from FIG. 3 that when the gonioscope 36 is inserted into the cup-shaped body 22 of the protective cover 20, the open upper end of the protective cover 20 is secured to the yoke 42 of the gonioscope 36 by a resilient ring 34, and the side wall 26 of the cup-shaped body 22 tightly fits to the outer surface of the gonioscope. However, a gap 23 must be left between the closed end of the protective cover and the eye-facing surface of the eye-contacting lens 40 in order to allow the material of the closed end of the cover to deform and to accommodate the gapless position between the concave surface of the eye-contacting lens and the substantially spherical surface of the eye. The cover-gonioscope system is now ready for use.

Figure 4:
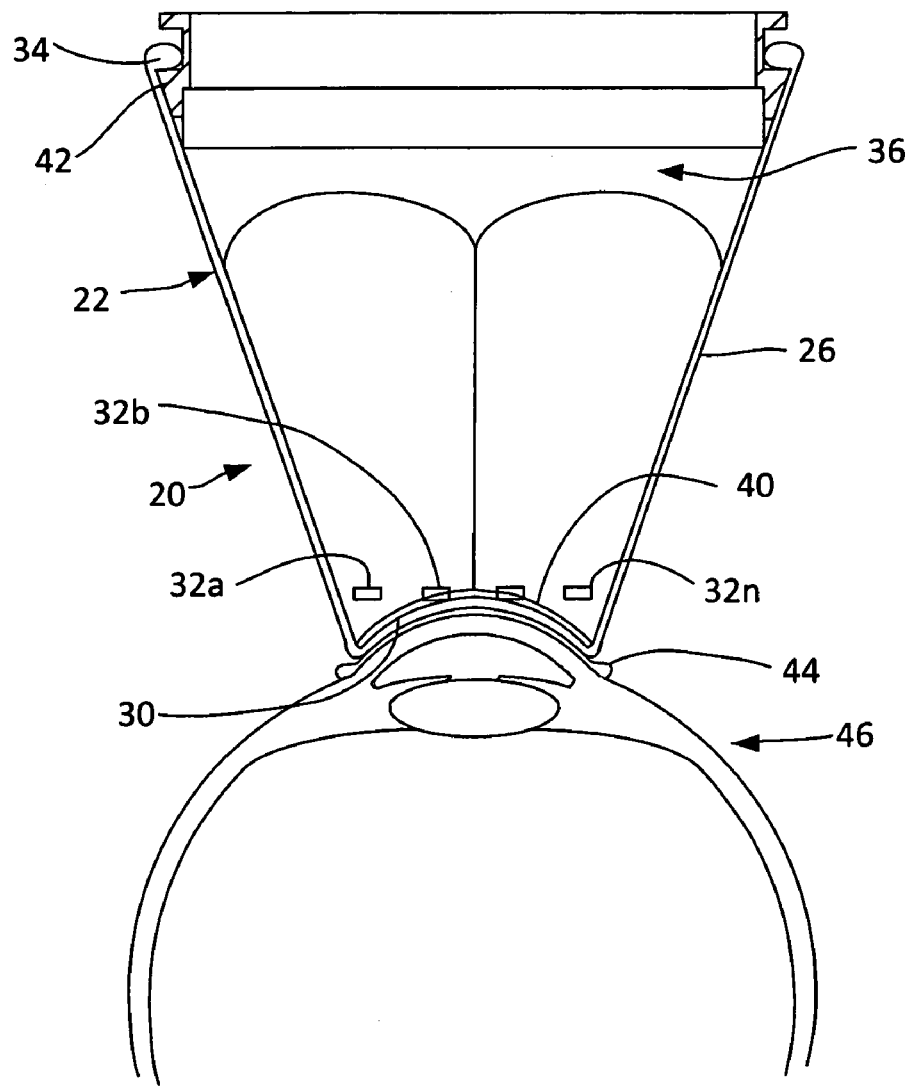
FIG. 4 is a longitudinal and sectional view of the protective cover in FIG. 3 in a working position, wherein the end face of the closed bottom portion of the protective cover accommodates the spherical shape of the eye with which is it in contact through the material of the bottom portion.

After appropriate preparation of the eye for examination or treatment, the eye-contacting lens 40 of the optical device 36 is brought in contact with the cornea 44 of the eye 46 through the material of the closed bottom portion 28 (FIG. 1). This condition is shown in FIG. 4, wherein the end face 30 of the closed bottom portion of the protective cover 22 accommodates the spherical shape of the eye that it contacts through the material of the bottom portion 28. If during fitting of the cover onto the optical device any air is trapped in the space between the closed bottom portion 28 and the eye-contacting lens 40, this air will be displaced from the aforementioned space through perforations 32a, 32b, 32n. In the condition shown in FIG. 4, the optical device is ready for use. After completion of observation or treatment, the protective cover 20 is discarded, while the end face of the eye-contacting lens 40 remains sterile and ready for repeated use.

Figure 5:
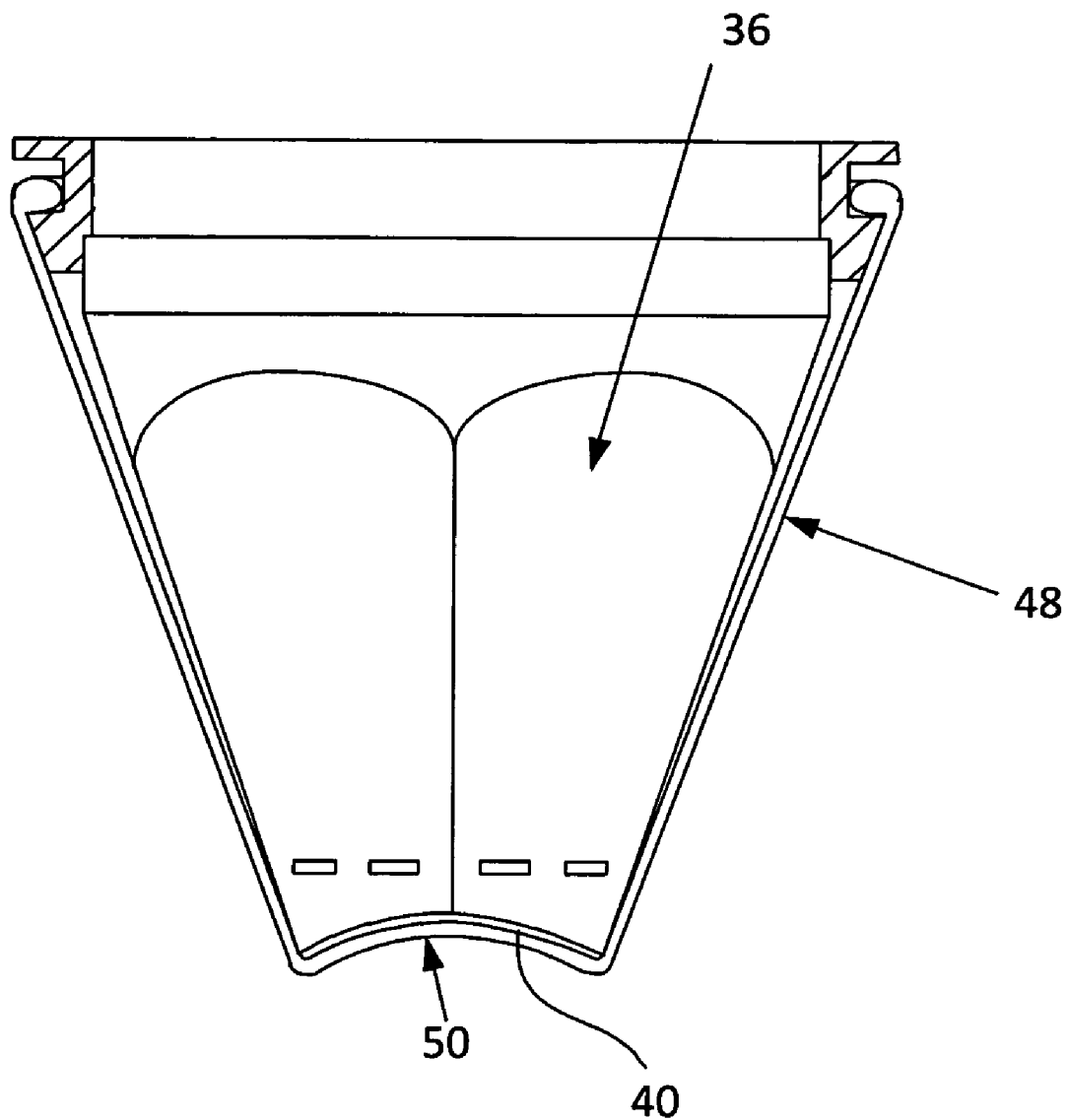
FIG. 5 is a longitudinal and sectional view of the protective cover made in accordance with another aspect of the invention wherein the bottom portion of the cover is molded flat so that it becomes flat under stretching that occurs when the disposable sterile protective cover is fitted onto the optical device prior to contact with the eye.

FIG. 5 shows a protective cover 48 made in accordance with another aspect of the invention. The protective cover 48, which is shown in the same position fitted on the optical device 36 (in the illustrated case, a gonioscope) as in FIG. 4, has the bottom portion 50 molded flat so that it becomes flat under stretching that occurs when the disposable sterile protective cover that is made from an elastic material is fitted onto the optical device 36 prior to contact with the eye. The remaining parts of the protective cover 48 remain the same as in the protective cover 22 shown in FIGS. 1 to 3.

In the modifications shown in FIGS. 1 to 5, the protective covers 22 and 48 are used merely for physically protecting the eye-contacting lens 40 of the optical device 36 from direct contact with the eye. The protective covers of these modifications have a uniform thickness, preferably in the range from 10 µm to 100 µm. Since the closed end portions of protective covers 22 and 48 have a thickness in the range of 10 µm to 100 µm, the refraction of light that occurs when the light beam passes through these portions of the covers can be neglected because the refraction of light will not affect the optical path of light.

Figure 6:
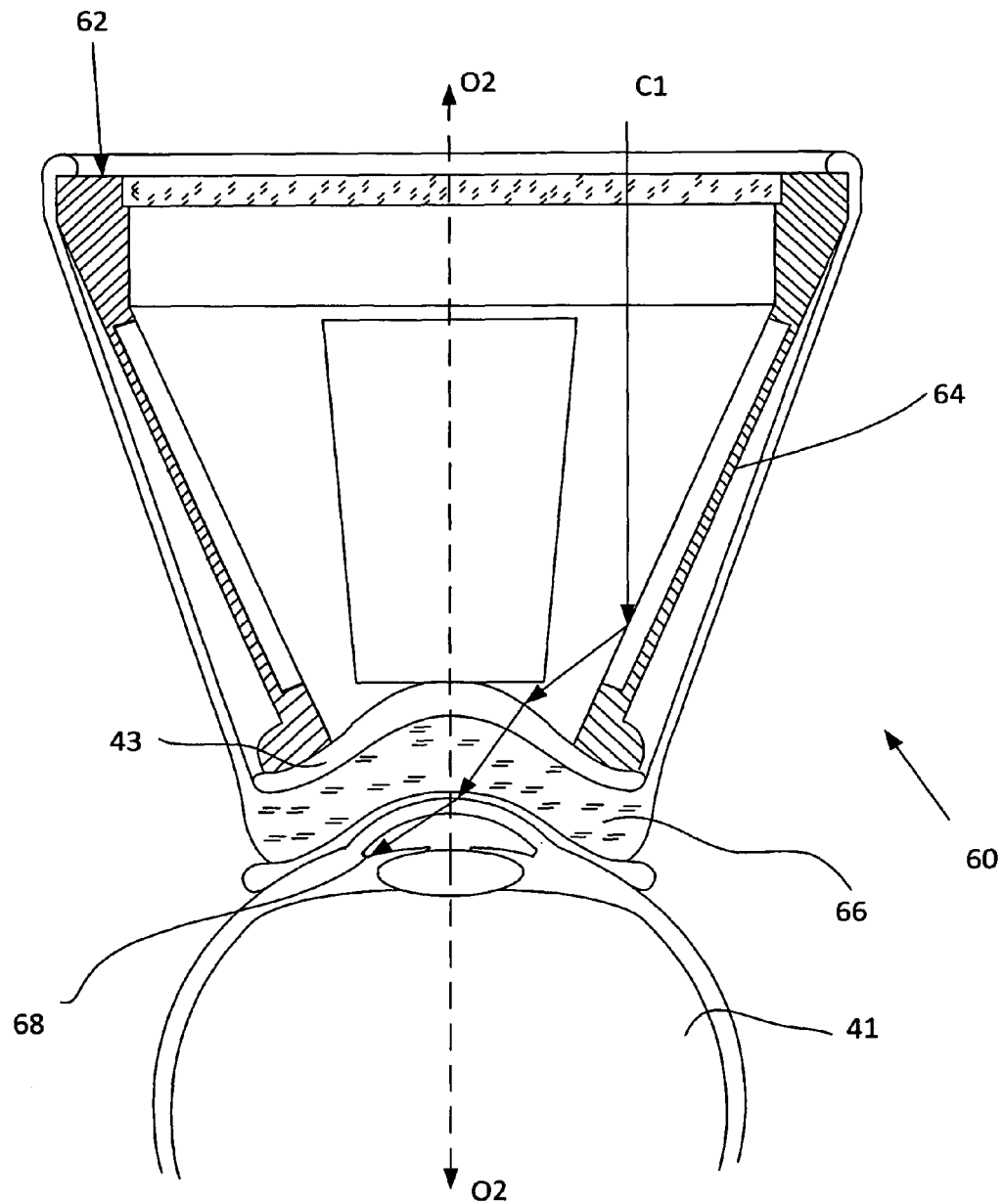
FIG. 6 is a longitudinal and sectional view of the protective cover for an optical device according to still another aspect of the invention, wherein the bottom portion of the cover is thicker than the remaining part of the cover body for both optical and protective functions.

A protective cover for an optical device according to still another aspect of the invention is shown in FIG. 6. The protective cover 60 of this modification combines the protective function with an optical function that changes the direction of the light so that it becomes possible to observe the light emitted from the pupil at angles that are smaller but close to the angle of full internal reflection from the pupil medium. In FIG. 6, the optical device 62 is a hollow gonioscope that is shown only for illustrative purposes.

As shown in FIG. 6, the protective cover 60 may have a thin side portion 64, e.g., of the same thickness as the protective cover of the previous modification, but the bottom portion 66 of cover 60 is thickened to a value sufficient for changing the direction of light due to refraction of light through this bottom portion 66 so as to direct the light to the hard-to-observe area 68 of the eye 41 (see light beam C1 in FIG. 6), such as the anterior chamber of the eye. For example, the thickness of the thickened bottom portion 66 (that during use of the optical device contacts the eye-contacting lens 43 of the gonioscope) can be in the range of 2 mm to 10 mm. In order to provide high index of refraction in combination with softness required for conforming to the patient's eye and low light absorption, it is recommended to manufacture the protective cover from the same materials as the protective covers of the previous modifications, which have a refraction index up to 1,4 and which satisfy all other conditions mentioned above. This makes it possible to observe the anterior chamber of the eye, which is very important for diagnosing glaucoma. In other words, the protective cover 60 and the optical device 62 form an optical system where line O2-O2 designates the optical axis of the system.

In fact, the provision of a thickened portion 66 that has an index of refraction greater than 1 increases the optical input aperture of the hollow optical device to the level of a monolithic prismatic gonioscope, thus making the hollow gonioscope suitable for viewing hard-to-observe portions inside the eye that otherwise are unattainable by hollow gonioscopes, per se.

In other words, for examination of more accessible parts of the eye, such as observation of the central parts of the retina, it is possible to use the protective cover 22, which is shown in FIG. 2. When it is necessary to observe areas of the eye such as the anterior chamber, e.g., for initial diagnosing of glaucoma, it is advantageous to use the protective cover 60, which is shown in FIG. 6.

It should be noted that the covers 22 and 60 of both types are disposable after use.

Although the invention has been shown and described with reference to specific embodiments, it is understood that these embodiments should not be construed as limiting the areas of application of the invention and that any changes and modifications are possible, provided that these changes and modifications do not depart from the scope of the attached patent claims. For example, although the optical device protected by the protective cover of the invention is shown in association with gonioscopes, the cover of the invention applies to optical devices of other types as well. Since the protective cover of the invention is intended for protection mainly of the surface of the eye-contacting lens (other surfaces of the optical device are not an issue), the side wall of the protective cover can be made in the form of strips, e.g., in the form of corrugated strips that possess springing properties and that raise the perforation above the eye-contacting lens when the protective cover is fitted onto the optical device.

The invention claimed is:

1. A disposable sterile protective cover for an optical device used in ophthalmology, said optical device having an outer diameter, the disposable sterile protective cover comprising a cup-shaped body made from a resilient material and having an open upper end with an inner diameter, a side wall, and a closed bottom portion, said inner diameter being smaller than the outer diameter of the optical device in order to secure the disposable sterile protective cover on the optical device due to resiliency of the transparent resilient material of the cup-shaped body, at least the closed bottom portion being made from a transparent material that is biologically acceptable for contact with the cornea of an eye when the optical device is brought into contact with an eye through the closed bottom portion, wherein the closed bottom portion has a concave end face intended for contact with the eye during use of said optical device and at least one perforation formed above said end face in the area that is beyond contact with the eye when the optical device is in use.

2. The disposable sterile protective cover according to claim 1, further comprising cover holding means formed on the open upper end for securing the cover to the optical device.

3. The disposable sterile protective cover according to claim 2, wherein the cover holding means comprise a resilient toroidal ring that comprises a thickened portion of said resilient material of the cup-shaped body.

4. The disposable sterile protective cover according to claim 1, wherein said transparent material that is biologically acceptable for contact with the cornea of the eye is selected from the group consisting of polyurethanes, isoprenes, polyisobutylenes, and optically clear silicone elastomers.

5. The disposable sterile protective cover according to claim 4, wherein said transparent material that is biologically acceptable for contact with the cornea of the eye has a refraction index of 1.4 or higher.

6. The disposable sterile protective cover according to claim 2, wherein said transparent material that is biologically acceptable for contact with the cornea of the eye is selected from the group consisting of polyurethanes, isoprenes, polyisobutylenes, and optically clear silicone elastomers.

7. The disposable sterile protective cover according to claim 6, wherein said transparent material that is biologically acceptable for contact with the cornea of the eye has a refraction index of 1.4 or higher.

8. The disposable sterile protective cover according to claim 3, wherein said transparent material that is biologically acceptable for contact with the cornea of the eye is selected from the group consisting of polyurethanes, isoprenes, polyisobutylenes, and optically clear silicone elastomers.

9. The disposable sterile protective cover according to claim 8, wherein said transparent material that is biologically acceptable for contact with the cornea of the eye has a refraction index of 1.4 or higher.

10. The disposable sterile protective cover according to claim 1, wherein said optical device used in ophthalmology has an eye-contacting lens for contact with the eye through said end face of the closed bottom portion.

11. The disposable sterile protective cover according to claim 10, wherein said transparent material that is biologically acceptable for contact with the cornea of the eye is selected from the group consisting of polyurethanes, isoprenes, polyisobutylenes, and optically clear silicone elastomers.

* * * * *